US006573102B2

(12) United States Patent
Li et al.

(10) Patent No.: US 6,573,102 B2
(45) Date of Patent: Jun. 3, 2003

(54) LYTIC REAGENT COMPOSITION FOR DETERMINATION OF NUCLEATED BLOOD CELLS

(75) Inventors: Yi Li, Miami, FL (US); Jing Li, Miami, FL (US)

(73) Assignee: Coulter International Corp., Miami, FL (US)

( * ) Notice: Subject to any disclaimer, the term of this patent is extended or adjusted under 35 U.S.C. 154(b) by 0 days.

(21) Appl. No.: 09/917,530

(22) Filed: Jul. 27, 2001

(65) Prior Publication Data

US 2003/0040115 A1 Feb. 27, 2003

(51) Int. Cl.[7] .............................................. G01N 31/00
(52) U.S. Cl. ................................ 436/17; 436/8; 436/10; 436/18; 436/63; 252/408.1; 435/2; 435/29
(58) Field of Search ................................. 436/8, 10, 17, 436/18, 63, 149, 150, 175; 252/408.1; 435/2, 4, 29, 34

(56) References Cited

U.S. PATENT DOCUMENTS

| | | | | |
|---|---|---|---|---|
| 4,286,963 A | * | 9/1981 | Ledis et al. | 436/18 |
| 4,528,274 A | | 7/1985 | Carter et al. | 436/10 |
| 5,116,539 A | * | 5/1992 | Hamaguchi et al. | 435/34 |
| 5,242,832 A | | 9/1993 | Sakata | 436/17 |
| 5,250,437 A | * | 10/1993 | Toda et al. | 436/10 |
| 5,298,426 A | | 3/1994 | Inami et al. | 436/63 |
| 5,389,549 A | * | 2/1995 | Hamaguchi et al. | 435/2 |
| 5,516,695 A | | 5/1996 | Kim et al. | 436/17 |
| 5,559,037 A | | 9/1996 | Kim et al. | 436/63 |
| 5,618,733 A | * | 4/1997 | Sakata et al. | 424/533 |
| 5,648,225 A | | 7/1997 | Kim et al. | 435/7.24 |
| 5,686,308 A | * | 11/1997 | Li et al. | 436/10 |
| 5,763,280 A | | 6/1998 | Li et al. | 436/66 |
| 5,786,224 A | * | 7/1998 | Li et al. | 435/2 |
| 5,817,518 A | * | 10/1998 | Li et al. | 252/408.1 |
| 5,834,315 A | * | 11/1998 | Riesgo et al. | 252/397 |
| 5,874,310 A | | 2/1999 | Li et al. | 436/10 |
| 5,882,933 A | | 3/1999 | Li et al. | 436/63 |
| 5,882,934 A | * | 3/1999 | Li et al. | 252/408.1 |
| 5,917,584 A | | 6/1999 | Li et al. | 356/39 |
| 6,210,969 B1 | * | 4/2001 | Li et al. | 252/408.1 |
| 6,214,625 B1 | * | 4/2001 | Li et al. | 252/408.1 |
| 6,410,330 B1 | * | 6/2002 | Li et al. | 422/73 |

FOREIGN PATENT DOCUMENTS

| EP | 1 004 880 A2 | 5/2000 |
|---|---|---|
| WO | 95/24651 | 9/1995 |

* cited by examiner

Primary Examiner—Maureen M. Wallenhorst
(74) Attorney, Agent, or Firm—Mitchell E. Alter

(57) ABSTRACT

A lytic reagent composition for measuring nucleated blood cells in a blood sample is described. The lytic reagent composition contains a quaternary ammonium surfactant, an ethoxylated phenol, and an ethoxylated alcohol. When mixed with a blood sample, the lytic reagent composition lyses red blood cells and enables a differentiation of nucleated red blood cells from other cell types by DC impedance measurement. The lytic reagent composition can further contain an organic ligand for determining total hemoglobin concentration of a blood sample photometrically. Further disclosed is a lytic reagent system including the lytic reagent composition and a diluent. In addition, a single reagent composition containing salts is also disclosed, which can be used without a separate diluent. The lytic reagent compositions can be used for concurrent measurement of nucleated red blood cells, WBC, and hemoglobin of a blood sample.

21 Claims, 7 Drawing Sheets

LYTIC REAGENT COMPOSITION FOR DETERMINATION OF NUCLEATED BLOOD CELLS

FIELD OF THE INVENTION

The present invention relates to a lytic reagent composition for determination of nucleated blood cells in a blood sample. More specifically the lytic reagent composition enables differentiation of nucleated red blood cells from other cell types in a blood sample by a direct current impedance measurement. In addition, the lytic reagent composition can further be used for measuring total hemoglobin concentration of the blood sample.

BACKGROUND OF THE INVENTION

Normal peripheral blood contains mature red blood cells which are free of nucleus. Nucleated red blood cells (NRBCs), or erythroblasts, are immature red blood cells. They normally occur in the bone marrow but not in peripheral blood. However, in certain diseases such as anemia and leukemia, NRBCs also occur in peripheral blood. Therefore, it is of clinical importance to measure NRBCs. Traditionally, differentiation and enumeration of NRBC are performed manually. The process involves the smearing of a blood sample on a microscope slide and staining the slide, followed by manual visual analysis of the individual slide. The NRBC concentration is reported as numbers of NRBC per 100 white blood cells. Usually, 200 white blood cells and the numbers of NRBC present in the same region on a blood smear are counted and the numbers are divided by 2 to express the NRBC concentration as the numbers of NRBC/100 WBC. This approach is extremely time-consuming as well as being subjective to the interpretation of the individual analyzing the slide.

In recent years, several fluorescence flow cytometry methods have been developed for differentiating NRBCs. These methods utilizes specific nuclear staining technique to distinguish NRBCs from other cell types because it is difficult to differentiate NRBCs based on their electronic or optical properties.

U.S. Pat. No. 5,298,426 (to Inami et al.) discloses a fluorescence method for differentiating NRBCs. The method utilizes a two-step staining using a first fluid which is an acidic hypotonic fluorescent dye solution, and a second fluid which changes the osmolality and pH of the first fluid. Inami et al. teaches that the first fluid contains an erythroblast-staining dye that diffuses into nucleated red blood cells to specifically stain their nuclei, and then separating a group of NRBCs from other cell groups on a two-dimensional plot whereby the results of NRBC differentiation are computed.

U.S. Pat. Nos. 5,516,695 and 5,648,225 (to Kim et al) disclose a multipurpose lysing reagent system and a method of use for subclassification of nucleated blood cells. The lysing reagent comprises a non-quaternary ammonium salt, an aliphatic aldehyde, a non-phosphate buffer which is inert to the aliphatic aldehyde, and a nuclear stain. The method comprises the steps of lysing a blood sample with the lysing reagent, incubating the sample mixture at an elevated temperature, and determining the nucleated blood cells including NRBCs with an automated electro-optical hematology instrumentation.

U.S. Pat. No. 5,559,037 (to Kim et al) discloses a method for flow cytometric analysis of NRBCs and leukocytes. The method comprises lysis of red blood cells and NRBC cytoplasm from a whole blood sample to expose the NRBC nuclei to a vital nuclear stain and minimizing the permeation of the vital nuclear stain into the leukocytes and analyzing the sample by measuring fluorescence and two angles of light scatter. Since leukocytes are also nucleated cells, staining of these cells needs to be prevented to avoid interference to the fluorescence measurement. The preservation of leukocyte membrane and minimizing the permeation of the nuclear stain into the leukocytes are achieved by concurrently fixing the leukocytes with an aliphatic aldehyde during lysis of red blood cells. The aldehyde fixatives are known as hazardous chemicals. In addition, the method requires heating of the reagent to 42° C. in order to obtain the NRBC and leukocyte differentiations.

EP 1 004 880 A2 discloses reagents and a method for discrimination and counting of nucleated red blood cells. The reagents include a hemolytic agent for dissolving red blood cells, and conditioning white blood cells and NRBCs in a sample to be suitable for staining; and at least one fluorescent dye selected to stain white blood cells and NRBCs differentially. The method includes the steps of lysing red blood cells, staining white blood cells and NRBCs, assaying the sample by measuring at least one scattered light parameter, and at least one fluorescence parameter.

U.S. Pat. No. 5,874,310 (to Li et al) discloses reagents and a method for differentiation of nucleated red blood cells. The method includes exposing a blood sample to a lysing reagent system to lyse mature red blood cells and analyzing the sample in a flow cell by two low angle light scatter measurements to differentiate NRBCs from other cell types. The method further includes a concurrent differentiation of white blood cells using electronic and optical analysis, wherein the electronic analysis is a DC impedance measurement.

U.S. Pat. No. 5,917,584 (to Li et al) discloses a method for differentiation of nucleated red blood cells. The method includes lysing mature red blood cells in a blood sample; analyzing the sample in a flow cell by two angles of light scatter measurement to differentiate NRBCs from other cell types, wherein the second light scatter signal is a medium angle or a right-angle light scatter signal.

The above described methods enable differentiation and enumeration of NRBCs and leukocytes by fluorescence flow cytometry and light scatter measurements. However, fluorescence and light scatter measurements are complex and expensive detection methods.

Many current non-fluorescence automated hematology analyzers, such as Abbott Cell-Dyn® 3500, COULTER® Gen*S™, Bayer Advia*120®, and Sysmex™ NE-9000 are only able to provide a NRBC flagging for the possible presence of NRBCs in an analyzed blood sample when the instruments sense an increased amount of signals near red blood cell debris area of an obtained cell distribution histogram. However, such methods are prone to generate false positive flaggings because many other blood abnormalities can cause increased signals at the same area, such as platelet clumps and sickle cells, as well as red cell debris from insufficiently lysed blood samples. In these methods NRBCs are not distinctly identified. Instead, only a common NRBC sample distribution pattern in a histogram or a dotplot is recognized by the instrument which can be confused with a similar pattern generated by above-mentioned other causes. For the flagged samples, including false positive flags, re-examination of the sample with manual method is required in clinical laboratories.

Furthermore, a well known problem with NRBC containing samples is erroneous white blood cell count (WBC)

reported by hematology analyzers on these samples. Since the nuclear volumes of NRBCs are close to those of white blood cells, the NRBCs are commonly counted as white blood cells on hematology analyzers which measure the sizes of blood cells, resulting an elevation of the WBC. Therefore, correction of NRBC contribution to the WBC reported from hematology analyzer is required for samples containing NRBC. Current practice in clinical laboratory is to subtract the numbers of NRBC obtained by manual count from the WBC reported by the hematology analyzers. This is time consuming and error prone.

In a different aspect, various lytic reagent compositions for analysis of white blood cells are known in the art. U.S. Pat. No. 5,618,733 (to Tsuji et al) discloses a reagent for analyzing leucocytes, which comprises an ionic surfactant; at least one organic compound having a hydrophobic group and an acidic group which has a negative charge in an aqueous solution for preserving leukocyte morphology by combining with a cationic component in leukocytes; a nonionic surfactant; and a buffer.

U.S. Pat. No. 4,528,274 (to Carter et al) discloses a lytic reagent for determination of at least two leukocyte populations in blood. The lytic reagent comprises an aqueous solution of at least two quaternary ammonium salts, and one non-cationic surfactant additive which includes nonionic polyoxyethylated alkylphenol. The prior art teaches that the quaternary ammonium salts and the additive are in sufficient amounts for positioning white blood cell populations relative to one another within the measurement time of the blood analyzer.

These lytic reagents enable differentiation of white blood cell subpopulations by preserving the morphology of white blood cells, or by controlling the size of the subpopulations. However, these reagents do not differentiate nucleated red blood cells from other cell types.

Furthermore, measurement of hemoglobin (Hgb) concentration of blood samples is an integral part of blood analysis, which is important for disease diagnosis and for monitoring responses to medical treatment. It is desirable to be able to accomplish multiple diagnostic analyses such as enumerating nucleated blood cells and measuring hemoglobin concentration of a blood sample using the same reagent and concurrent detections.

Among the many well known methods for hemoglobin determination, the cyanmethemoglobin method has been recommended as a standard by the International Committee for Standardization in Hematology. However, the presence of cyanide in the reagent waste has caused enormous environmental concern. In last ten years, a tremendous effort has been given to develop automated hemoglobin analysis methods without utilizing cyanide.

U.S. Pat. No. 5,242,832 (to Sakata) discloses a cyanide-free lysing reagent for counting white blood cells and measuring the hemoglobin concentration in a blood sample. The lysing reagent comprises at least one first surfactant which is a quaternary ammonium salt, at least one second surfactant which includes cationic and amphoteric surfactants, and at least one hemoglobin stabilizer selected from the group including Tiron, 8-hydroxyquinoline, bipyridine, 1–10-phenanthroline, phenolic compounds, bisphenol, pyrazole and derivatives, second phenyl 5-pyrazolone and derivatives, phenyl 3-pyrazolone, and imidazole and its derivatives.

PCT/US95/02897 (to Kim) discloses a cyanide-free method and reagent for determining hemoglobin in a whole blood sample. The reagent comprises a ligand selected from the group consisting of imidazole and derivatives, N-hydroxyacetamide, H-hydroxylamine, pyridine, oxazole, thiazole, pyrazole, pyrimidine, purine, quinoline and isoquinoline, and a surfactant with a strong erythrolytic capability selected from the group consisting of lauryl dimethylamine oxide and octylphenoxy polyethoxyethanol. The analysis method is fast, less than 10 seconds. However, the reagent only performs under an extreme alkaline condition, pH from 11 to 14. In addition, no capability of counting leukocytes, nor differentiating nucleated red blood cells from other cell types is taught by Kim.

U.S. Pat. No. 5,763,280 (to Li et al) discloses cyanide-free reagents for measuring hemoglobin in a blood sample, counting leukocytes, and differentiating leukocyte subpopulations. The reagent comprises a hemolytic surfactant selected from the group consisting of quaternary ammonium salts, pyridinium salts, organic phosphate esters, and organic sulfonates to lyse erythrocytes and release hemoglobin, and an organic ligand selected from the group consisting of triazole and its derivatives, tetrazole and its derivatives, alkali metal salts of oxonic acid, melamine, aniline-2-sulfonic acid, quinaldic acid, 2-amino-1,3,4-thiadiazole, triazine and its derivatives, urazole, DL-pipecolinic acid, isonicotinamide, anthranilonitrile, 6-aza-2-thiothymine, adenine, 3-(2-thienyl)acrylic acid, benzoic acid and alkali metal and ammonium salts of benzoic acid, and pyrazine and its derivatives to form a stable chromogen with hemoglobin.

U.S. Pat. No. 5,882,934 (to Li et al) also discloses cyanide-free reagents for measuring hemoglobin in a blood sample, counting leukocytes, and differentiating leukocyte subpopulations. The reagents further comprise salts, in addition to hemolytic surfactants and organic ligands, for adjusting conductivity of the reagents for impedance measurement. However, none of the above described cyanide-free reagent and hemoglobin measurement methods enables differentiation of nucleated red blood cells from other cell types, and enumeration of nucleated red blood cells in a blood sample.

Based on foregoing, there exist a need for a reagent that enables simple and less costly analysis method for differentiating and enumerating nucleated red blood cells. Furthermore, it is desirable to have a multifunctional reagent enabling enumeration of nucleated blood cells, differentiation of nucleated red blood cells from other cell types, and measurement of hemoglobin concentration in the absence of cyanide.

SUMMARY OF THE INVENTION

The present invention relates to a lytic reagent composition for lysing red blood cells, and measuring nucleated blood cells in a blood sample. The lytic reagent composition comprises at least one quaternary ammonium surfactant, an ethoxylated phenol, and an ethoxylated alcohol, and having a pH ranging from about 2 to about 11. When mixed with a blood sample prediluted by a diluent, the lytic reagent composition lyses red blood cells and enables a differentiation of nucleated red blood cells from other cell types by DC impedance measurement.

The lytic reagent composition can further comprise an organic ligand in a sufficient amount to form a chromogen with hemoglobin for determining total hemoglobin concentration of a blood sample by measuring spectrophotometric absorbance at predetermined wavelengths.

The present invention further relates to a lytic reagent system for measuring nucleated blood cells in a blood sample, which comprises a lytic reagent composition and a diluent. The lytic reagent composition comprises at least one quaternary ammonium surfactant, an ethoxlyated phenol, and an ethoxylated alcohol, and having a pH ranging from about 2 to about 11. The diluent is a neutral aqueous solution comprising a salt or salts to adjust conductivity of the diluent sufficient for an impedance measurement, and an antimicrobial agent. The lytic reagent system can further comprise an organic ligand either in the lytic reagent composition or in the diluent for measuring hemoglobin concentration of a blood sample.

In a further embodiment, the present invention also relates to a lytic reagent composition comprising at least one quaternary ammonium surfactant, an ethoxlyated phenol, an ethoxylated alcohol, and a salt or salts to adjust the conductivity of the lytic reagent composition sufficient for impedance measurement. The lytic reagent composition can further comprise an organic ligand for hemoglobin measurement. This lytic reagent composition can be used for a combined diluting and lysing, and preparing a blood sample for measuring nucleated blood cells in one step.

DETAILED DESCRIPTION OF THE INVENTION

Figure 1A:
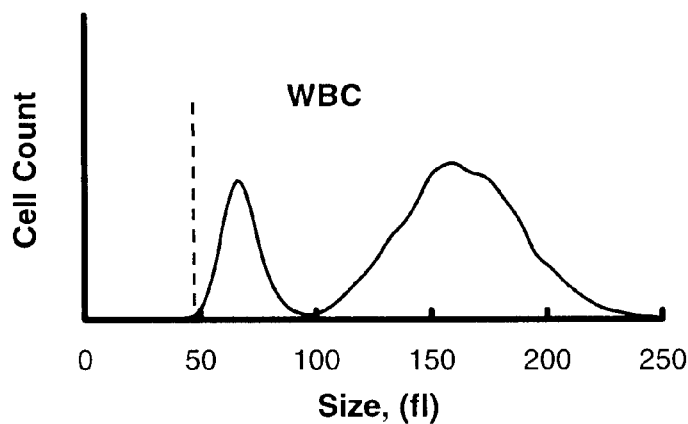
FIGS. 1A, 1B and 1C are the DC histograms of whole blood samples processed according to the procedure described in Example 1 using the lytic reagent composition of Example 1 of the present invention.

In one embodiment the present invention is directed to a lytic reagent composition for measurement of nucleated blood cells. More specifically the lytic reagent composition enables differentiation of nucleated red blood cells from other cell types in a blood sample by DC impedance measurement. The nucleated blood cells in this context can include nucleated red blood cells and white blood cells.

The lytic reagent composition comprises an aqueous solution of:

(a) a quaternary ammonium salt or salts, represented by following molecular structure:

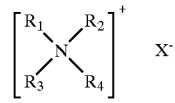

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;

(b) an ethoxylated alkyl phenol, wherein the alkyl group has 6 to 12 carbon atoms, and the number of ethylene oxide is in a range from about 10 to about 50; and (c) an ethoxylated alcohol represented by following molecular structure:

wherein $R_1$ is an alkyl, alkenyl or alkynyl group having 10 to 22 carbon atoms, $R_2$ is —O—, and n is between 20 and 35.

The pH of the lytic reagent composition is in a broad range from about 2 to about 11.

Quaternary ammonium salt functions to lyse red blood cells and cell membranes of nucleated blood cells. The concentration of a quaternary ammonium salt in the lytic reagent composition needs to be in an amount sufficient to lyse red blood cells while preserving nuclear volumes of nucleated blood cells. With the lytic reagent composition described above, red blood cells of a sample are completely lysed upon mixing with the lytic reagent composition. The cell membranes of the nucleated red blood cells (NRBC) are lysed, and the sizes of their nuclei are small. However, the white blood cell membranes are partially lysed, and their remaining sizes are relatively larger. When the concentration of a quaternary ammonium salt is too high, white blood cells will further shrink, and the sizes of lymphocytes will be very close to that of NRBCs. Consequently, the NRBCs and white blood cells will not be differentiable when measured by their sizes. When the concentration of a quaternary ammonium salt is too low, red blood cells will not be completely lysed, and they can interfere the detection of nucleated blood cells. Moreover, lysed cell membrane debris can also interfere the detection if they are not dissolved or sufficiently reduced in size. The concentration of the quaternary ammonium salt in the lytic reagent composition ranges from about 6 g/L to about 50 g/L, preferably, from about 10 g/L to about 40 g/L.

On the other hand, it is known that the lytic potency of quaternary ammonium salt increases with the length of the R1 group. A quaternary ammonium salt having a 16 carbon chain tends to shrink the nucleated blood cells more than the those having 12 or 14 carbon chains. To achieve optimal separation of NRBCs from the white blood cells, a proper carbon chain length of R1 group has been determined. Preferably, tetradecyltrimethyl ammonium salt, or a mixture of tetradecyltrimethyl ammonium salt with hexadecyltrimethyl ammonium salt or dodecyltrimethyl ammonium salt is used.

The ethoxylated phenol in the lytic reagent composition is found to improve the separation between the NRBCs and the white blood cells by preserving the size of lymphocytes. In addition, the ethoxylated phenol also assists to solubilize cell membrane debris, and reduces the possibility of interference. The number of ethylene oxide in the ethoxylated phenol is preferably in a range from about 20 to about 40. The concentration of the ethoxylated phenol in the lytic reagent composition is in a range from about 2 g/L to about 40 g/L.

The ethoxylated alcohol in the lytic reagent composition is also found to preserve the size of lymphocytes. It has been discovered that a combination of ethoxylated alcohol and ethoxylated phenol provides better separation between the NRBCs and the lymphocytes than using either the ethoxylated alcohol or the ethoxylated phenol alone. Therefore, a combination of ethoxylated phenol and ethoxylated alcohol is used. The concentration of the ethoxylated alcohol in the lytic reagent composition is in a range from about 1 g/L to about 20 g/L.

Suitable examples of ethoxylated alcohol are Plurofac A38 prill surfactant, from BASF Corp., New Jersey, and Hetoxol STA-30, from Heterene, Inc., New Jersey. A suitable example of ethoxylated phenol is Igepal SS-837, from Rhône-Poulenc, New Jersey.

Optionally, the lytic reagent composition can further comprise preservatives, such as antioxidants, in an amount sufficient for extending shelf life of the reagent. A suitable example of anti-oxidant is butylmethylphenol. The preservatives need to be compatible with the primary functional components of the lytic reagent composition.

In another embodiment, the lytic reagent composition can further comprise an organic ligand for hemoglobin measurement. As described above, the lytic reagent composition of the present invention lyses red blood cells upon mixing with a blood sample, which releases hemoglobin into the sample mixture. In the presence of an organic ligand, the released hemoglobin can form a chromogen, which can be measured photometrically. Suitable examples of organic ligands include tetrazole and its derivatives such as 5-amino tetrazole; imidazole and its derivatives such as methylimidazole, and ethylimidazole; quinaldic acid; and benzoic acid and alkali metal salts of benzoic acid.

In the presence of an organic ligand, the lytic reagent composition can be used for both measuring nucleated blood cells and hemoglobin measurement. Such multifunctional feature is advantageous for its application on automated hematology analyzers since a fewer numbers of reagents and sample preparation steps are required.

The concentration of the organic ligand in the lytic reagent composition needs to be sufficient to enable formation of a stable hemoglobin chromogen. The concentration varies with the ligand type, depending on the affinity of the ligand to hemoglobin. In general, if the amount of ligand in the lytic reagent composition is not sufficient, the formed hemoglobin chromogen could be unstable. The concentration of the organic ligand in the lytic reagent composition is in a range from about 1 g/L to about 10 g/L.

The concentrations of the chemical components in the lytic reagent composition are the concentrations under conditions in which the nucleated blood cell enumeration and hemoglobin measurement are accomplished with the use of a suitable blood diluent for the convenience of using the existing blood analyzers. However, the concentrations of the chemical components can be changed depending upon the volume ratio between the lytic reagent composition and the diluent.

In a further embodiment the present invention is directed to a reagent system used for measurement of nucleated blood cells. The reagent system comprises (I) a lytic reagent composition comprising an aqueous solution of:
(a) a quaternary ammonium salt or salts, represented by following molecular structure:

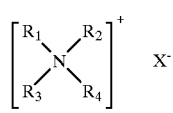

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;

(b) an ethoxylated alkyl phenol, wherein the alkyl group has 6 to 12 carbon atoms, and the number of ethylene oxide is in a range from about 10 to about 50; and (c) an ethoxylated alcohol represented by following molecular structure:

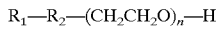

wherein $R_1$ is an alkyl, alkenyl or alkynyl group having 10 to 22 carbon atoms, $R_2$ is —O—, and n is between 20 and 35; and the pH of the lytic reagent composition is in a range from about 2 to about 11; and (II) a diluent.

The lytic reagent composition of the reagent system has been described above. Additionally, the lytic reagent composition can further comprise an organic ligand for hemoglobin measurement as described previously.

The diluent is an aqueous solution, which comprises (a) a salt or salts to adjust conductivity of the diluent sufficient for an impedance measurement, and (b) an antimicrobial agent. Suitable examples of salts are alkali metal salts. Preferably, sodium or potassium sulfate, chloride, phosphate or citrate is used in the diluent.

A blood diluent is commonly used on a hematology analyzer to dilute a blood sample for measurements of red blood cells also. In the latter case, isotonic diluent is required to maintain the red blood cell volume. Therefore, for a combined use for measurements of red blood cells and nucleated blood cells, it is preferable that the blood diluent is adjusted to be isotonic, although isotonicity is not required for measuring the nucleated blood cells.

The diluent can further comprise a buffer. Variety of organic and inorganic buffers can be used in the diluent. Similar to the conductivity discussed above, since the diluent is commonly used for red blood cell measurements, which requires a neutral pH, the diluent is preferred to be neutral.

The antimicrobial agent needs to be in a sufficient amount to preserve the diluent, but not interfering with the functions of the lytic reagent.

Alternatively, an organic ligand for hemoglobin measurement can be added into the diluent, instead of included in the lytic reagent composition.

To use the lytic reagent composition of the present invention for measuring nucleated blood cells and differentiating NRBC from other cell types, a blood sample is diluted by a suitable blood diluent, then a sufficient amount of the lytic reagent composition is added and mixed with the diluted sample in a chamber by mechanical or bubble mixing to form a sample mixture (the dilution ratio of the total reagent volume versus blood is about 250:1.) About seven to nine seconds after the addition of the lytic reagent composition, the sample mixture is drawn through a non-focus aperture by vacuum and measured with a DC detector. The DC detector detects electrical signals generated as remaining nucleated blood cells pass through the aperture due to impedance change. A cell size distribution histogram is obtained from the measurement. Furthermore, a count of the total nucleated cells in the sample mixture can be also generated by DC impedance measurement.

Alternatively, a focused flow cell can also be used for DC impedance measurement. When a focused flow cell is used, the sample dilution ratio is lower because a sheath fluid used for focusing will further reduce the number of cells measured in the flow cell. It is found that a dilution ratio about 30:1 to about 35:1 can be used for the lytic reagent composition of the present invention in this case.

FIG. 1A shows a histogram of a fresh normal whole blood sample obtained using a lytic reagent composition of Example 1, following the process detailed in the Example 1. As shown, nucleated blood cells, all white blood cells in this case, have a bimodal distribution. Majority of the population in the peak on the left is lymphocytes. However, it has been observed that other white cell populations can also fall into this region. On the left side of this peak, there is a clear area, and no cells appear in this region.

Figure 1B:
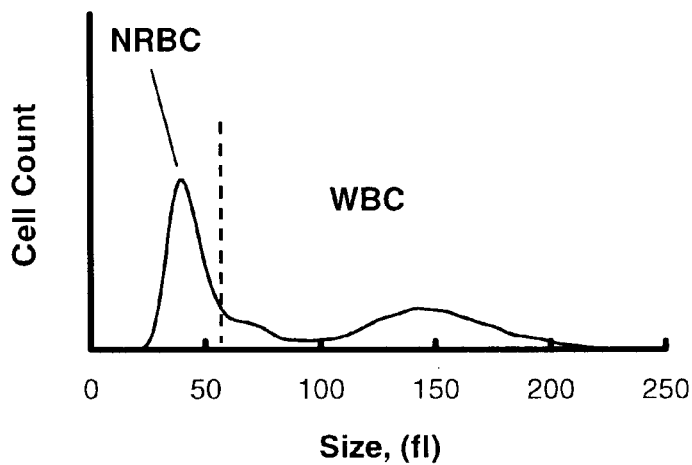
Figure 1C:
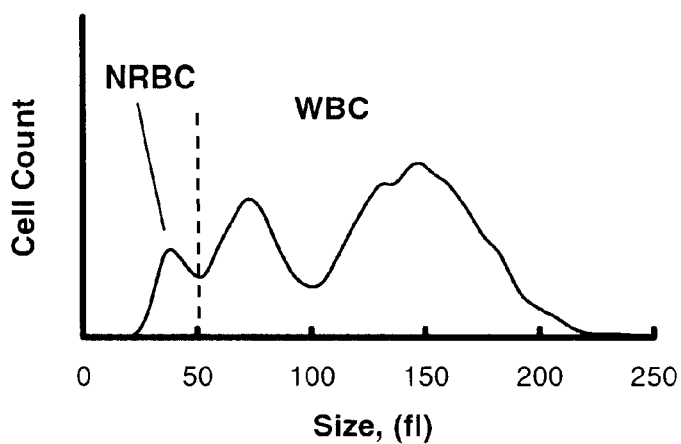

FIGS. 1B and 1C show histograms obtained using the same lytic reagent composition and following the same process from two clinical whole blood samples which contained nucleated red blood cells (reported by the manual reference method). As shown, an additional peak from the nucleated red blood cells (NRBC) appeared on the left side of the white blood cells. Apparently, the nuclei of the nucleated red blood cells had smaller sizes in comparison to that of white blood cells, under the reaction condition described. Such a separation in sizes achieved by utilizing the lytic reagent composition of the present invention enables differentiation of the nucleated red blood cells from white blood cells using the one dimensional histogram obtained from the DC impedance measurement.

Using the lytic reagent composition of the present invention, since NRBC population is differentiated from other cell types, the presence of NRBC population in a sample can be identified and reported. To report the presence of clinically abnormal populations in a blood sample is often called flagging on hematology analyzers, which is an important feature for assisting clinical diagnosis.

Furthermore, using the lytic reagent composition of the present invention the NRBC population can be enumerated. When the threshold of a DC detector is set below the size of NRBCs as shown in the figures, the NRBC population can be enumerated together with white blood cells. After differentiating the NRBC population from other cell types based on the population distribution of an obtained DC histogram, NRBC concentration of an analyzed sample can be calculated. The NRBC concentration can be reported as the numbers of NRBC per hundred of white blood cells (NRBC/100 WBC), which is the same unit of the manual reference. Alternatively, the numbers of NRBC can also be reported as an absolute number per unit volume of a blood sample. In this case, the number of NRBC per 100 white blood cells is multiplied by the white blood cell count of the same sample.

Moreover, as described previously, historically when white blood cells are measured by size, NRBCs are counted, or partially counted with white blood cells since they are not differentiated from other nucleated blood cells. The interference caused by NRBCs can result in elevated and erroneous white blood cell counts. With the lytic reagent composition of the present invention, upon differentiating the NRBCs, the contribution of this population to the white blood cell count can be subtracted from the total count of nucleated blood cells to provide a corrected white blood cell count.

Figure 2:
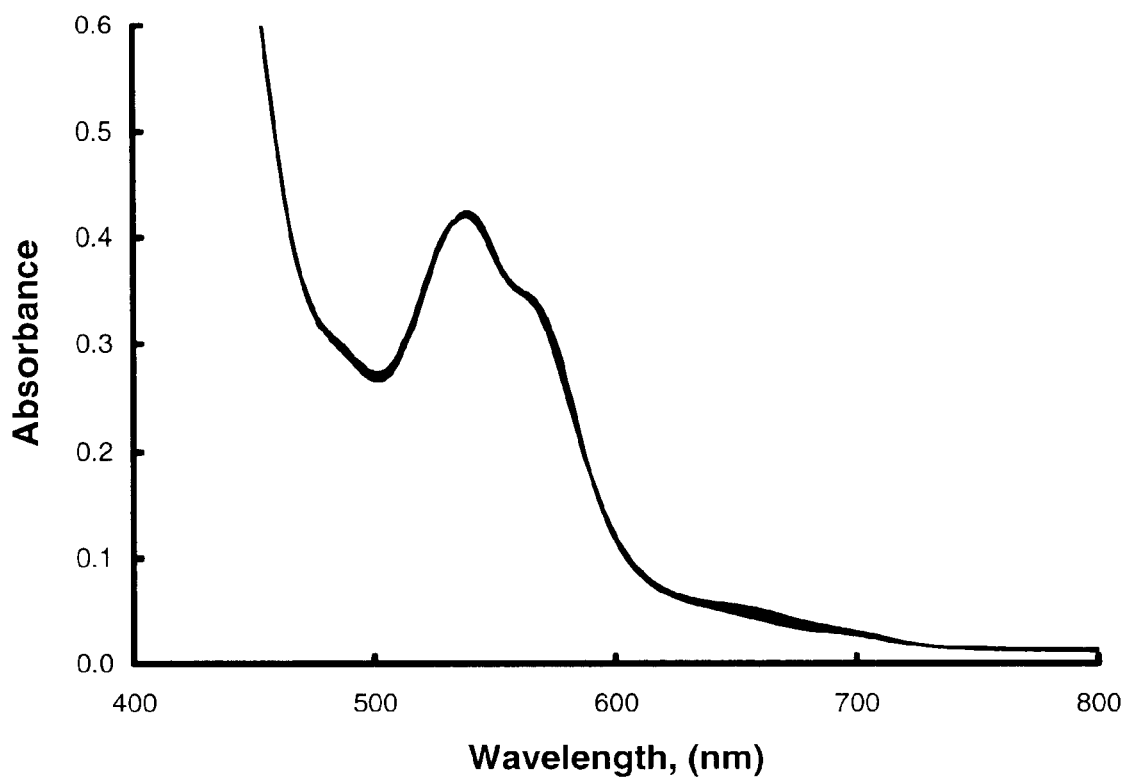
FIG. 2 shows a series of absorption spectra of a blood sample processed according to the procedure of Example 2 using the lytic reagent composition of Example 2. Total of twelve spectra were acquired in 120 seconds with a 10 second interval.

FIG. 2 shows a series of hemoglobin photometric absorption spectra of a whole blood sample obtained using the lytic reagent composition of the present invention which further contains an organic ligand, and processed with a manual procedure detailed in Example 2. A total of twelve spectra were acquired in 120 seconds with a 10 second interval. As shown, the hemoglobin chromogen formed had a maximum absorption at about 538 nm with a shoulder at about 565 nm. The hemoglobin chromogen formed rapidly after mixing the lytic reagent composition with the prediluted sample. As illustrated by a complete overlap of continuously acquired spectra, the hemoglobin chromogen was very stable during 120 seconds of analysis, which was far beyond a typical data acquisition time used on a hematology analyzer.

Figure 3A:
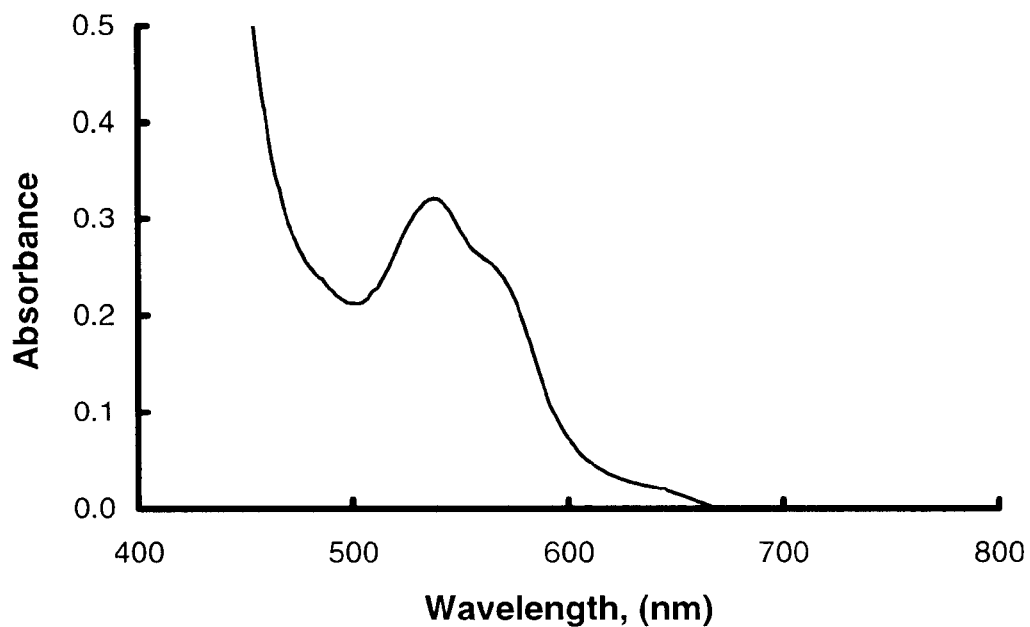
FIG. 3A shows a spectrum of a whole blood sample treated according to the procedure described in Example 3, using the lytic reagent and diluent compositions of Example 3.
Figure 3B:
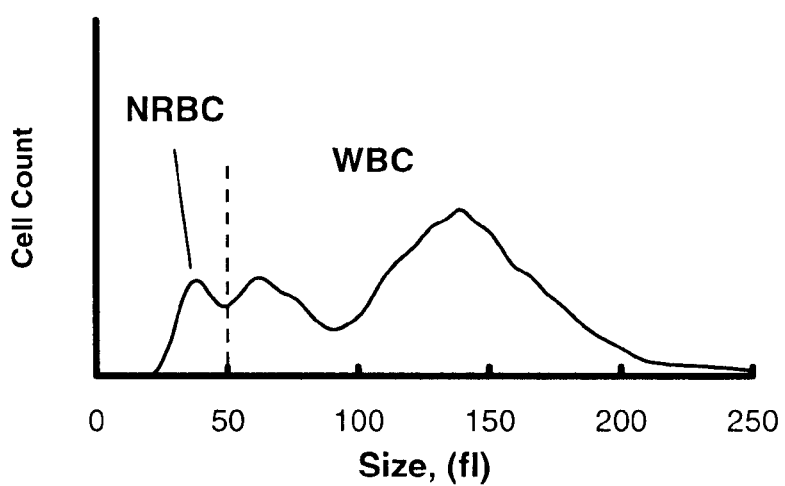
FIG. 3B shows a histogram of a clinical whole blood sample obtained according to the procedure described in Example 1 using the lytic reagent and diluent compositions of Example 3.

As described previously, an organic ligand for hemoglobin measurement can be added into either the lytic reagent composition or the diluent of the lytic reagent system. FIGS. 3A and 3B illustrate results of the later alternative, wherein the diluent contains an organic ligand.

FIG. 3A is a spectrum of a whole blood sample treated using the lytic reagent composition of the present invention and diluent composition described in Example 3, which contains imidazole as a hemoglobin ligand. FIG. 3B shows a histogram of a clinical blood sample containing NRBC, obtained using the lytic reagent and diluent compositions of Example 3. The histogram clearly shows differentiation of nucleated red blood cells from the white blood cells.

The lytic reagent composition of the present invention enable enumeration of white blood cells, enumeration of nucleated red blood cells, and hemoglobin measurement with one sample preparation.

Example 4 demonstrates utility of the lytic reagent composition in analyzing clinical samples. Totally 95 normal and 74 clinical whole blood samples containing nucleated red blood cells were analyzed on an experimental hematology analyzer with the instrument configuration detailed in Example 1, using the lytic reagent composition of Example 2 and Isoton® III (Beckman Coulter, Inc. Miami, Fla.) as diluent. The same samples were also analyzed on COULTER® GEN*S hematology analyzer, and COULTER COUNTER® ZBI as references. The numbers of NRBC per 100 WBC were obtained from a 500 cell manual count following NCCLS standard method, and used as reference.

The DC histogram obtained on the experimental hematology analyzer was analyzed by an experimental algorithm to differentiate the nucleated red blood cells from the white blood cells, and to report the numbers of NRBC per 100 WBC. Then the NRBCs were subtracted from the total nucleated blood cells measured to obtain a corrected WBC count.

Figure 4A:
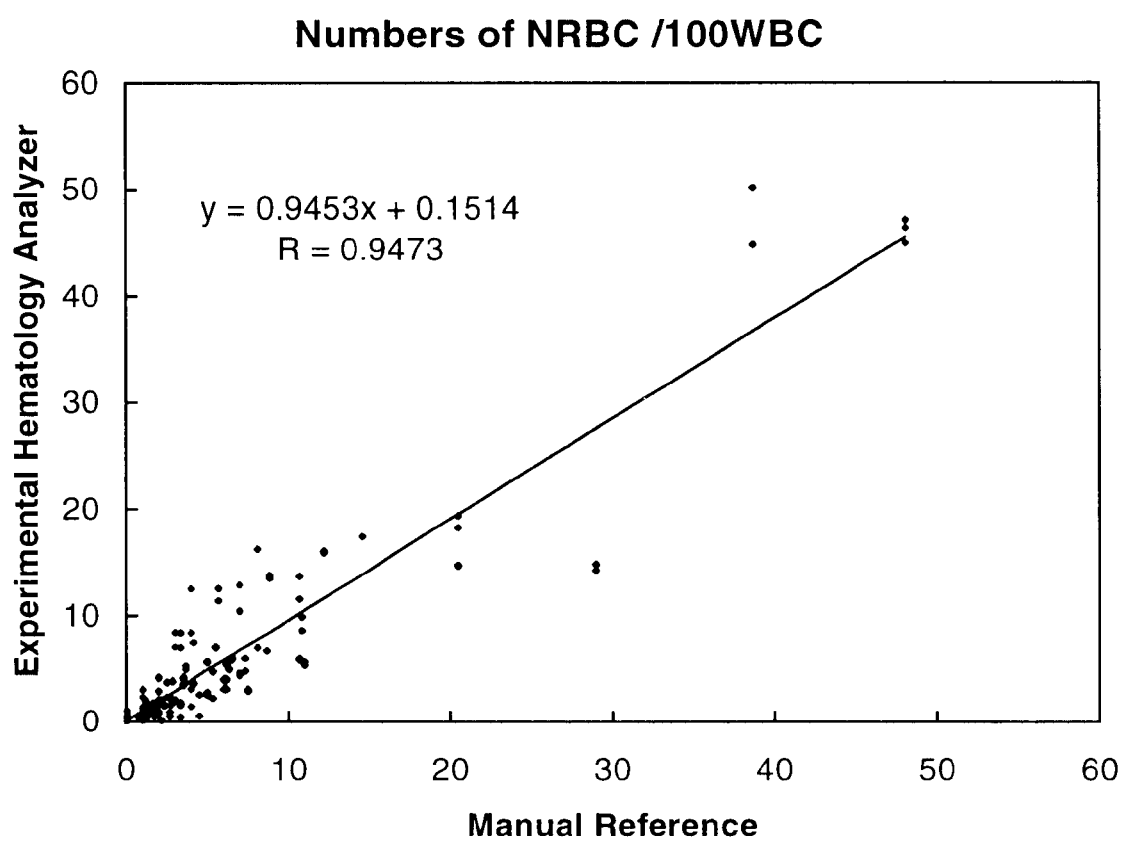
FIG. 4A shows the correlation of NRBC concentration obtained by using the lytic reagent composition and method of the present invention described in Example 4 to the manual reference results.

FIG. 4A shows the results of NRBC enumeration, which demonstrates a good linear correlation between the results obtained using the lytic reagent composition of the present invention and the manual reference.

Figure 4B:
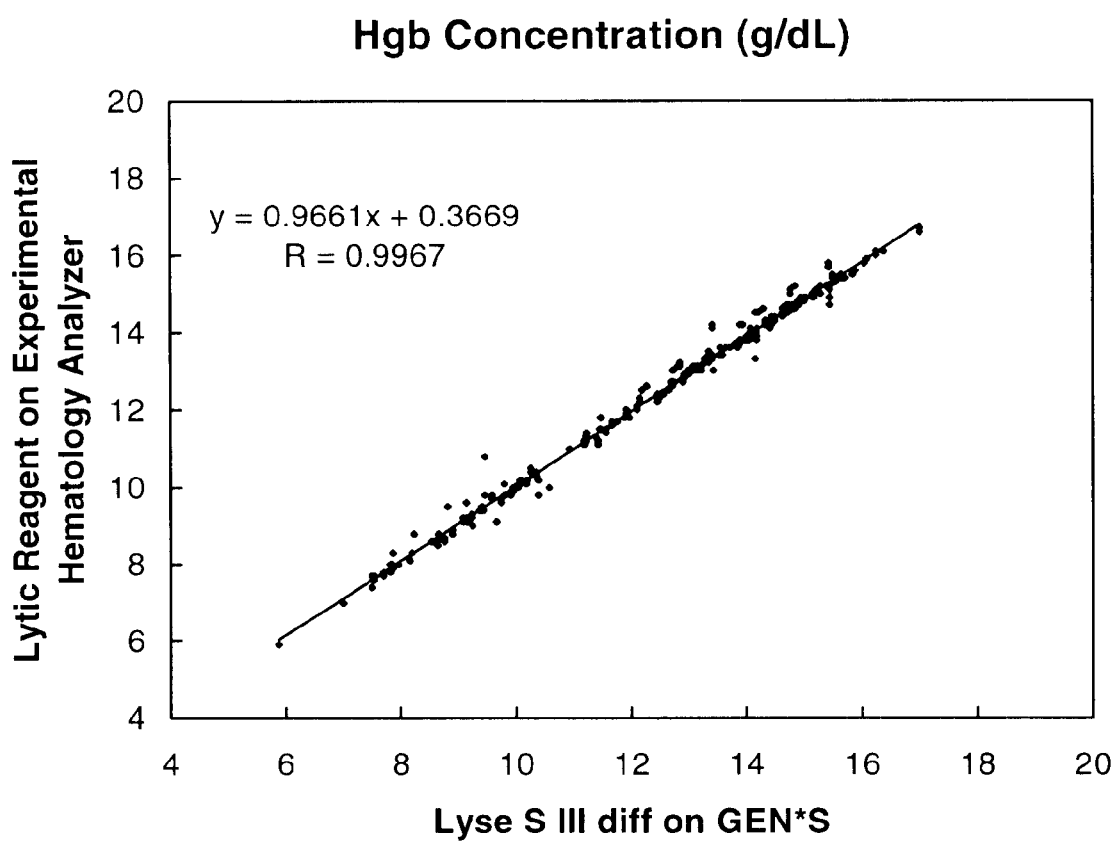
FIG. 4B shows the correlation of the hemoglobin concentration obtained using the lytic reagent composition of the present invention described in Example 4 to that obtained using Lyse S® III diff on COULTER Gen*S.

FIG. 4B shows the correlation between hemoglobin concentration obtained by using the lytic reagent composition of the present invention and that obtained on COULTER® GEN*S. The results demonstrate an excellent linear correlation for hemoglobin measurement.

Figure 4C:
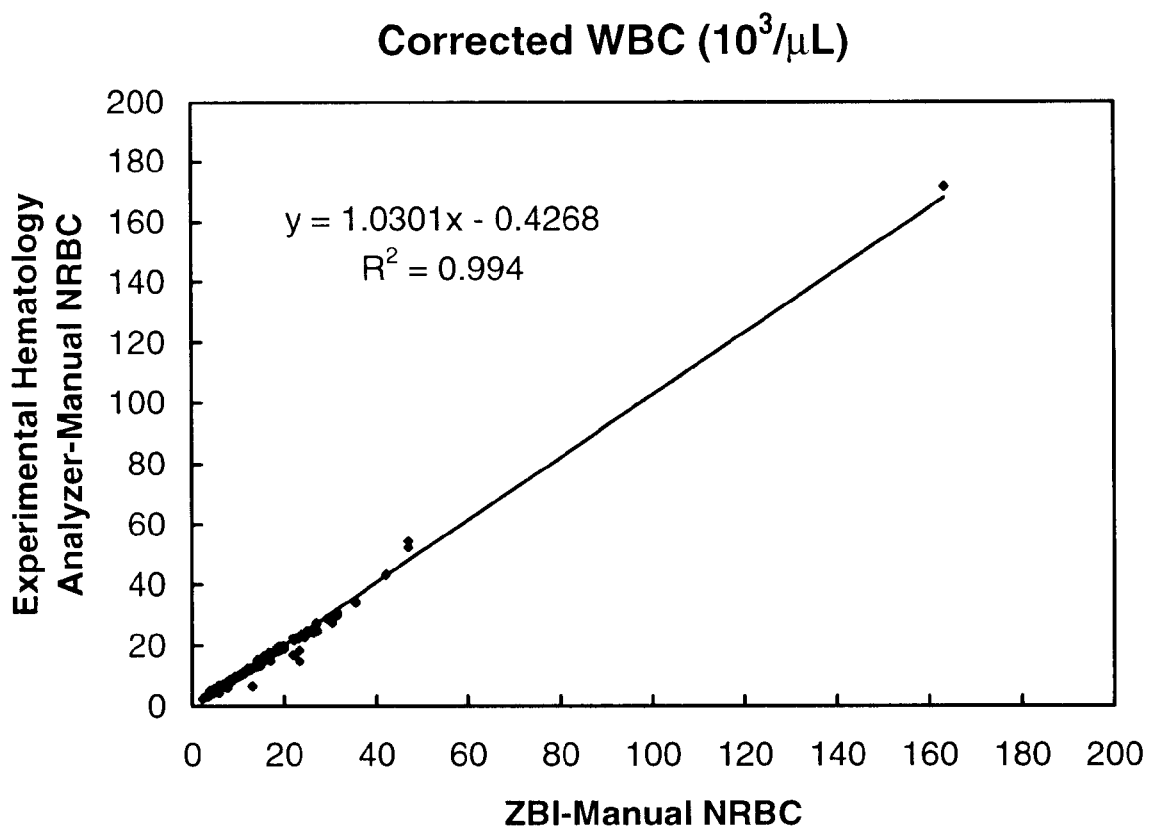
FIG. 4C shows the correlation of corrected WBC count obtained using the lytic reagent composition and method of the present invention described in Example 4 to the corrected WBC count obtained by correcting the count obtained on COULTER COUNTER® ZBI with manual NRBC count.

FIG. 4C shows the correlation of the corrected WBC count between the reference and the results obtained by using the lytic reagent composition of the present invention.

The reference results were obtained by subtracting the manual NRBC results from the WBC count obtained on the COULTER COUNTER® ZBI. As shown, the results obtained by using the lytic reagent composition of the present invention correlates excellently to the reference.

In an additional embodiment, the present invention relates to a single reagent composition for combined diluting and lysing a blood cell sample without pre-dilution by a diluent. If a hematology analyzer employs a single reagent, without predilution by a diluent, one can reduce the concentrations of the chemical ingredients of the lytic reagent composition of the present invention, and adjust conductivity of the lytic reagent composition to enable its use for impedance measurements. The conductivity can be adjusted by addition of a sufficient amount of a salt, or salts. Suitable examples of salts are alkali metal salts, such as sulfates, chlorides, phosphates, and citrates. In a single reagent composition, the concentrations of the chemical components of the lytic reagent composition should be the same as the concentrations contained in the final sample mixture when separate lytic reagent and diluent are used. If a concurrent hemoglobin measurement is desired, the single reagent composition can further contain an organic ligand described above.

Figure 5A:
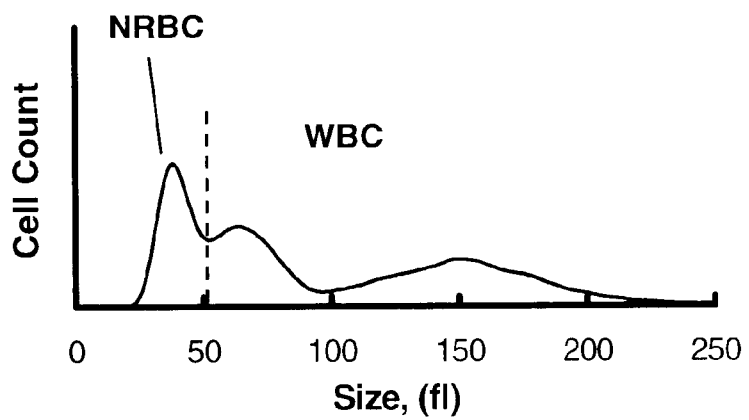
FIG. 5A shows a histogram of a whole blood sample obtained according to the procedure described in Example 5 using the single reagent composition of Example 5.
Figure 5B:
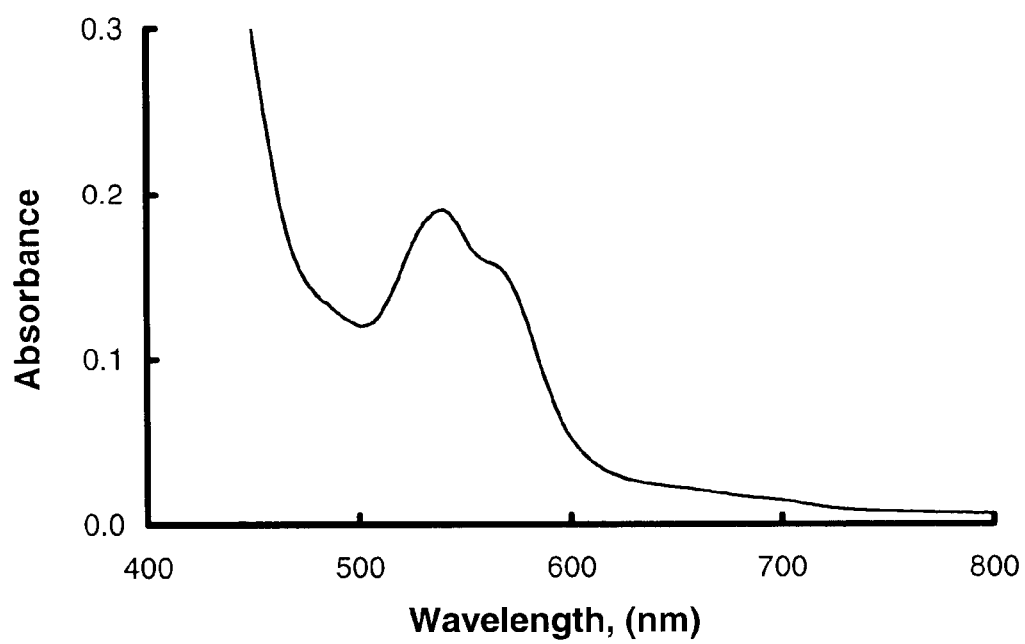
FIG. 5B shows a spectrum of the same sample processed with the single reagent composition of Example 5 according to the procedure described in Example 5.

FIGS. 5A and 5B illustrate utility of a single reagent composition for combined diluting and lysing a blood sample for measuring nucleated blood cells and hemoglobin. FIG. 5A shows a DC histogram of a clinical whole blood sample containing NRBC, obtained on an experimental hematology analyzer which used a single reagent composition of Example 5 as both the lytic reagent and diluent. The histogram clearly shows differentiation of NRBC from the white blood cells.

FIG. 5B shows a photometric absorption spectrum of a whole blood sample treated with the single reagent composition. The spectrum shows the same characteristic hemoglobin chromogen obtained by using a separate lytic reagent composition and a diluent.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

A reagent of the following composition was prepared.

| | |
|---|---|
| tetradecyltrimethylammonium bromide | 25.0 g |
| Igepal SS-837 (from RhÔne-Poulenc) | 15.0 g |
| Plurofac A38 prill surfactant (from BASF Corp.) | 4.0 g |
| distilled water adjusted to 1 liter | |
| pH | 5.0 |

28 μl of a whole blood sample was aspirated by an experimental hematology analyzer, diluted with 6 ml of Isoton® III (Beckman Coulter, Inc. Miami, Fla.), then mixed with 1 ml of above lytic reagent composition to lyse red blood cells. The sample mixture was drawn through a set of three non-focused flow apertures (arranged in parallel). The apertures had a length of 120μ and a width of 100μ. The nucleated blood cells were counted by a DC impedance measurement, and a histogram of the blood cells, after pulse editing, was also produced (averaged from the measurements of three apertures).

FIG. 1A shows a histogram of a fresh normal blood sample analyzed following above procedure, which shows a bi-module distribution of the white blood cells. FIGS. 1B and 1C show two clinical abnormal samples analyzed following the above procedure. The clinical samples contain 230 NRBC/100 WBC, and 9 NRBC/100 WBC, respectively. As seen, a distinct population of NRBC appears on the left side of the white blood cells. The NRBC population was differentiated from the white blood cells, and the ratio between the NRBC and white blood cells (×100) was reported as the numbers of NRBC/100 WBC. Alternatively, the NRBC can also be reported as absolute count in an unit volume of the blood sample by incorporating the total count of white blood cells.

EXAMPLE 2

A reagent of the following composition was prepared.

| | |
|---|---|
| tetradecyltrimethylammonium bromide | 25.0 g |
| Igepal SS-837 (from RhÔne-Poulenc) | 15.0 g |
| Plurofac A38 prill surfactant (from BASF Corp.) | 4.0 g |
| tetrazole | 2.0 g |
| BHT (predissolved in ethanol) | 0.04 g |
| distilled water adjusted to 1 liter | |
| pH | 2.9 |

11.6 μl of a whole blood sample was diluted by 2500 μl of Isoton® III, then 403 μl of above lytic reagent composition was mixed manually with the prediluted sample. The photometric absorption spectrum of the sample was measured immediately on a Beckman DU 7500 spectrophotometer. FIG. 2 shows the spectra of the blood sample processed according to the above procedure. FIG. 2 is an overlay of totally twelve spectra. The first spectrum was acquired at 10 seconds after the addition of the lytic reagent composition, and then one spectrum was acquired every 10 seconds automatically, with the last one acquired at 130 seconds after addition of the lytic reagent composition.

EXAMPLE 3

The reagents of the following compositions were prepared.

| | |
|---|---|
| Lytic reagent | |
| tetradecyltrimethylammonium bromide | 25.0 g |
| Igepal SS-837 (from RhÔne-Poulenc) | 15.0 g |
| Plurofac A38 prill surfactant (from BASF Corp.) | 4.0 g |
| distilled water adjusted to 1 liter | |
| pH | 5.0 |
| Diluent | |
| $Na_2SO_4$ | 10.58 g |
| NaCl | 3.0 g |
| $Na_2EDTA$ | 1.5 g |
| imidazole | 1.5 g |
| 6N HCl added to adjust pH to neutral | |
| distilled water adjusted to 1 liter | |
| pH | 7.1 |
| Osmolality | 308 mOsm |

11.6 μl of a fresh normal whole blood sample was diluted by 2500 μl of above diluent, then 403 μl of the above lytic reagent composition was mixed manually with the prediluted sample. The photometric absorption spectrum of the sample was measured immediately on a Beckman DU 7500 spectrophotometer. FIG. 3A shows the spectrum of the blood sample processed according to the above procedure.

A clinical whole blood sample containing 19 NRBC/100 WBC was analyzed on the experimental hematology analyzer described in Example 1 with the same instrument configuration except using non-focused flow apertures of 120μ length by 100μ width, and using the lysing reagent and diluent of Example 3. FIG. 3B shows the obtained histogram, which clearly illustrates differentiation of nucleated red blood cells from white blood cells.

EXAMPLE 4

95 normal and 74 clinical whole blood samples containing NRBCs were analyzed on the experimental hematology analyzer described in Example 1 using the lytic reagent composition of Example 2 and Isoton® III as diluent. The absorption of a sample mixture was also measured at 525 nm on the analyzer immediately after measuring the nucleated blood cells. Hemoglobin concentration of the sample was reported by the analyzer. Then the same samples were also analyzed on a COULTER® GEN*S hematology analyzer, and on a COULTER COUNTER® ZBI. The COULTER® GEN*S was operated under its standard configuration according to manufacturer's manual, using Lyse S® III diff (Beckman Coulter, Inc. Miami, Fla.) as lysing reagent and Isoton® III as diluent. The white blood cells of the blood samples were counted on COULTER COUNTER® ZBI following the NCCLS reference procedure for WBC count. The threshold on COULTER COUNTER® ZBI was set at 7.5 to ensure nucleated red blood cells being counted. A 500 cell manual count was obtained by three medical technologists for all clinical samples as a reference for nucleated red blood cells, and reported as numbers of nucleated red blood cells observed per 100 WBC counted (no. NRBC/100 WBC).

The DC histogram obtained was analyzed by an experimental algorithm to differentiate the NRBCs from the white blood cells, and to report the numbers of NRBC per 100 WBC. Then the NRBCs were subtracted from the total nucleated blood cells counted to obtain a correct WBC count.

FIG. 4A shows the results of NRBC enumeration obtained following the above process versus manual reference. The correlation coefficients, slopes and intercepts of the regression lines showed a good linear correlation for NRBC.

FIG. 4B shows the correlation between hemoglobin concentration obtained by using the above lytic reagent on the experimental hematology analyzer and that obtained on COULTER® GEN*S. The result demonstrates an excellent linear correlation for hemoglobin concentration.

FIG. 4C shows the correlation between the corrected WBC count obtained using the above lytic reagent on the experimental hematology analyzer and the procedure described above, and obtained by subtracting the manual NRBC results from the WBC count obtained on COULTER COUNTER® ZBI. The result illustrates an excellent correlation between the method of the present invention and the reference method.

EXAMPLE 5

A reagent of the following composition was prepared.

| | |
|---|---|
| tetradecyltrimethylammonium bromide | 3.48 g |
| Igepal SS-837 (from RhÔne-Poulenc) | 2.09 g |
| Plurofac A38 prill surfactant (from BASF Corp.) | 0.56 g |

-continued

| | |
|---|---|
| tetrazole | 0.28 g |
| $Na_2SO_4$ | 7.94 g |
| NaCl | 3.46 g |
| $Na_2EDTA$ | 0.09 g |
| ADA | 1.21 g |
| antimicrobials | 0.98 g |
| BHT (predissolved in ethanol) | 0.01 g |
| distilled water adjusted to 1 liter | |
| pH | 5.8 |
| Osmolality | 312 mOsm |

A clinical whole blood sample containing 31 NRBC/100 WBC was analyzed on the experimental hematology analyzer described in Example 1 with the same instrument configuration, but using the above single reagent composition as both lysing reagent and diluent. FIG. 5A shows the obtained histogram, which illustrates differentiation of nucleated red blood cells from white blood cells.

Additionally, 11.6 μl of the same sample was diluted and mixed by 2903 μl of the above single reagent composition. The photometric absorption spectrum of the sample was measured immediately on a Beckman DU® 7500 spectrophotometer. FIG. 5B shows the obtained spectrum, which has the same characteristic hemoglobin chromogen obtained by using a separate lytic reagent composition and a diluent.

We claim:

1. A lytic reagent composition for lysing red blood cells, and measuring nucleated blood cells consisting essentially of an aqueous solution of:

(a) at least one quaternary ammonium salt, represented by following molecular structure:

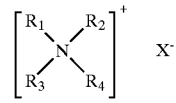

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;

(b) an ethoxylated alkyl phenol having an alkyl group with 6 to 12 carbon atoms, and between about 10 to about 50 ethylene oxide groups; and (c) an ethoxylated alcohol represented by following molecular structure:

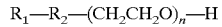

wherein $R_1$ is an alkyl, alkenyl or alkynyl group having 10 to 22 carbon atoms, $R_2$ is —O—, and n is between 20 and 35; and wherein pH of said lytic reagent composition is in a range from about 2 to about 11; and said lytic reagent composition enables differentiation of nucleated red blood cells from other cell types.

2. The lytic reagent composition of claim 1 wherein said at least one quaternary ammonium salt has a concentration ranging from about 6 g/L to about 50 g/L.

3. The lytic reagent composition of claim 1 wherein said at least one quaternary ammonium salt is tetradecyltrimethylammonium bromide.

4. The lytic reagent composition of claim 1 wherein said ethoxylated phenol has a concentration in a range from about 2 g/L to about 40 g/L.

5. The lytic reagent composition of claim 1 wherein said ethoxylated alcohol has a concentration in a range from about 1 g/L to about 20 g/L.

6. A cyanide-free lytic reagent composition for lysing red blood cells and measuring nucleated blood cells and hemoglobin concentration comprising an aqueous solution of:
(a) at least one quaternary ammonium salt, represented by following molecular structure:

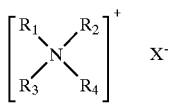

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;
(b) an ethoxylated alkyl phenol having an alkyl group with 6 to 12 carbon atoms, and between about 10 to about 50 ethylene oxide groups;
(c) an ethoxylated alcohol represented by following molecular structure:

wherein $R_1$ is an alkyl, alkenyl or alkynyl group having 10 to 22 carbon atoms, $R_2$ is —O—, and n is between 20 and 35; and
(d) an organic ligand in a sufficient amount to form a chromogen with hemoglobin for measuring hemoglobin concentration of a blood sample,
wherein pH of said lytic reagent composition is in a range from about 2 to about 11.

7. The lytic reagent composition of claim 6 wherein said organic ligand is selected from the group consisting of (a) tetrazole and its derivatives, (b) imidazole and its derivatives, (c) quinaldic acid, and (d) benzoic acid and alkali metal salts of benzoic acid.

8. The lytic reagent composition of claim 7 wherein said organic ligand has a concentration in a range from about 1 g/L to about 10 g/L.

9. The lytic reagent composition of claim 7 wherein said organic ligand is tetrazole and its derivatives.

10. A reagent system for lysing red blood cells, and measuring nucleated blood cells comprising:
(I) a lytic reagent composition consisting essentially of an aqueous solution of:
(a) at least one quaternary ammonium salt, represented by following molecular structure:

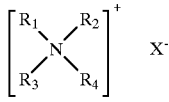

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;
(b) an ethoxylated alkyl phenol having an alkyl group has with 6 to 12 carbon atoms, and between about 10 to about 50 ethylene oxide groups; and
(e) an ethoxylated alcohol represented by following molecular structure:

wherein $R_1$ is an alkyl, alkenyl or alkynyl group having 10 to 22 carbon atoms, $R_2$ is —O—, and n is between 20 and 35; and
wherein pH of said lytic reagent composition is in a range from about 2 to about 11; and said lytic reagent composition enables differentiation of nucleated red blood cells from other cell types; and
(II) a diluent.

11. A reagent system of claim 10 wherein said diluent is an aqueous solution comprising:
(a) at least one salt in an amount to adjust conductivity of said diluent sufficient for an impedance measurement; and
(b) an antimicrobial agent.

12. The reagent system of claim 11 wherein said diluent further comprises an organic ligand in a sufficient amount to form a chromogen with hemoglobin for measuring hemoglobin concentration of a blood sample.

13. The reagent system of claim 12 wherein said organic ligand is selected from the group consisting of (a) tetrazole and its derivatives, (b) imidazole and its derivatives, (c) quinaldic acid, and (d) benzoic acid and alkali metal salts of benzoic acid.

14. The reagent system of claim 11 wherein said diluent further comprises a buffer to adjust pH of said diluent to neutral.

15. A lytic reagent composition for lysing red blood cells, and measuring nucleated blood cells consisting essentially of an aqueous solution of:
(a) at least one quaternary ammonium salt, represented by following molecular structure:

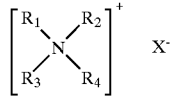

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;
(b) an ethoxylated alkyl phenol having an alkyl group with 6 to 12 carbon atoms, and between about 10 to about 50 ethylene oxide groups;
(c) an ethoxylated alcohol represented by following molecular structure:

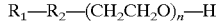

wherein $R_1$ is an ethyl, alkenyl or alkynyl group having 10 to 22 carbon atoms, $R_2$ is —O—, and n is between 20 and 35; and
(d) at least one salt in an amount to adjust conductivity of said lytic reagent composition sufficient for an impedance; and
wherein said lytic reagent composition enables differentiation of nucleated red blood cells from other cell types.

16. The lytic reagent composition of claim 15 wherein said at least one salt is selected from the group consisting of alkali metal salts of sulfate, chloride, phosphate, and citrate.

17. The lytic reagent composition of claim 15 wherein said at least one quaternary ammonium salt is tetradecyltrimethylammonium bromide.

18. A cyanide-free lytic reagent composition for lysing red blood cells, and measuring nucleated blood cells and hemoglobin concentration of a blood sample comprising an aqueous solution of:

(a) at least one quaternary ammonium salt, represented by following molecular structure:

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;

(b) an ethoxylated alkyl phenol having an alkyl group with 6 to 12 carbon atoms, and between about 10 to about 50 ethylene oxide groups;

(c) an ethoxylated alcohol represented by following molecular structure:

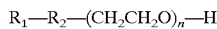

wherein $R_1$ is an alkyl, alkenyl or alkynyl group having 10 to 22 carbon atoms, $R_2$ is —O—, and n is between 20 and 35;

(d) at least one salt in an amount to adjust conductivity of said lytic reagent composition sufficient for an impedance measurement; and (e) an organic ligand in a sufficient amount to form a stable chromogen with hemoglobin for measuring hemoglobin concentration of said blood sample.

19. The lytic reagent composition of claim 18 wherein said organic ligand is selected from the group consisting of (a) tetrazole and its derivatives, (b) imidazole and its derivatives, (c) quinaldic acid, and (d) benzoic acid and alkali metal salts of benzoic acid.

20. A cyanide-free reagent system for lysing red blood cells, and measuring nucleated blood cells and hemoglobin concentration of a blood sample comprising:

(I) a lytic reagent composition comprising an aqueous solution of:

(a) at least one quaternary ammonium salt, represented by following molecular structure:

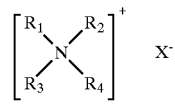

wherein $R_1$ is an alkyl, alkenyl or alkynyl group having 12 to 16 carbon atoms; $R_2$, $R_3$ and $R_4$ are alkyl groups having 1 to 4 carbon atoms and $X^-$ is chloride or bromide anion;

(b) an ethoxylated alkyl phenol having an alkyl group with 6 to 12 carbon atoms, and between about 10 to about 50 ethylene oxide groups; and (e) an ethoxylated alcohol represented by following molecular structure:

wherein $R_1$ is an alkyl, alkenyl or alkynyl group having 10 to 22 carbon atoms, $R_2$ is —O—, and n is between 20 and 35; and d) an organic ligand in a sufficient amount to form a chromogen with hemoglobin for measuring hemoglobin concentration of said blood sample, wherein pH of said lytic reagent composition is in a range from about 2 to about 11; and (II) a diluent.

21. The reagent system of claim 20 wherein said organic ligand is selected from the group consisting of (a) tetrazole and its derivatives, (b) imidazole and its derivatives, (c) quinaldic acid, and (d) benzoic acid and alkali metal salts of benzoic acid.

* * * * *